United States Patent [19]

Lichstein

[11] 3,952,584
[45] Apr. 27, 1976

[54] MEASUREMENT OF ABSORBENCY CHARACTERISTICS OF ABSORBENT STRUCTURES

[76] Inventor: Bernard M. Lichstein, 887 Colonia Road, Elizabeth, N.J. 07208

[22] Filed: Mar. 4, 1975

[21] Appl. No.: 555,101

[52] U.S. Cl. .................................................. 73/73
[51] Int. Cl.² ........................................ G01N 13/00
[58] Field of Search ................ 73/64.3, 73, 74, 159

[56] References Cited
UNITED STATES PATENTS

| | | | |
|---|---|---|---|
| 1,561,285 | 11/1925 | Sesler | 73/73 |
| 2,545,281 | 3/1951 | Hunt | 73/73 |

*Primary Examiner*—James J. Gill
*Assistant Examiner*—John S. Appleman

[57] ABSTRACT

An apparatus and method is provided for simultaneously measuring the liquid absorbent capacity and the wetting rate of absorbent structures as a function of volume and time. These absorbency characteristics can be measured at a zero or a negative hydrostatic head, where the absorbency characteristics are due only to the liquid drawing power of the absorbent structure, or at a positive hydrostatic head. The device comprises: a liquid reservoir for holding a column of liquid where the reservoir has an opening at its bottom and is closed at the top; an orifice plate having a liquid delivery orifice which is in flow communication with the opening in the reservoir through a flow communication means; an air bleed orifice in the liquid reservoir between the top and bottom thereof and in fluid communication with the atmosphere; and a means for adjusting the relative heights of the air bleed orifice to the orifice plate. When the liquid is introduced into the reservoir and the flow communication means, the relative height of the orifice plate to the air bleed orifice may be adjusted so that there is no fluid driving force acting to cause liquid to flow through the liquid delivery orifice. When an absorbent material is placed over the liquid delivery orifice in contact with the fluid and the fluid is drawn into the absorbent material, the liquid system will be balanced so that in the absence of the absorbent material there will be no flow through the orifice plate. Measurements can be made on multiple plied structures, with the structures held at any angle from 0° to 90° to the horizontal, with the source of the liquid coming from either below or above the structure and with the structure being subjected to no load or to compressive loads. The method and apparatus can be used to determine the absorbency characteristics of absorbent structures with respect to different liquids.

11 Claims, 7 Drawing Figures

U.S. Patent   April 27, 1976   3,952,584
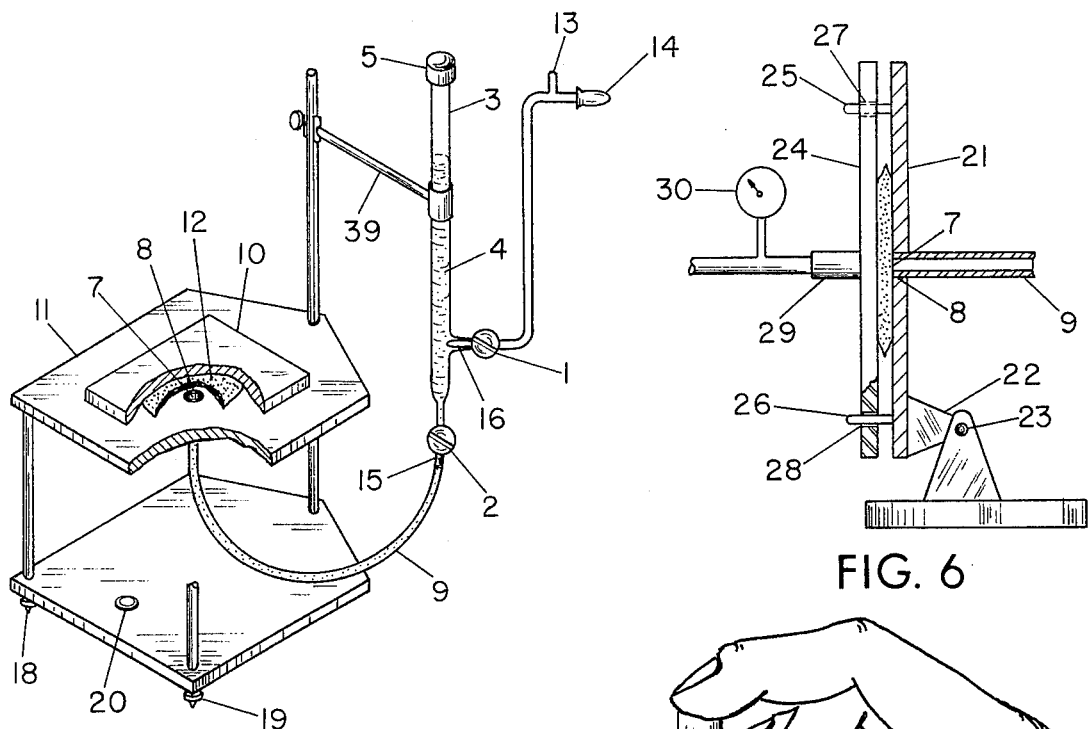
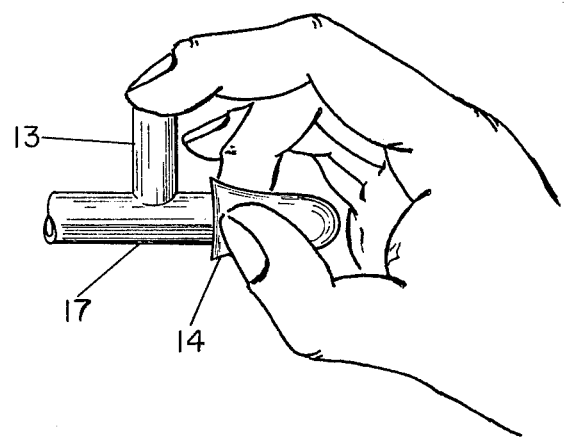
FIG. 6
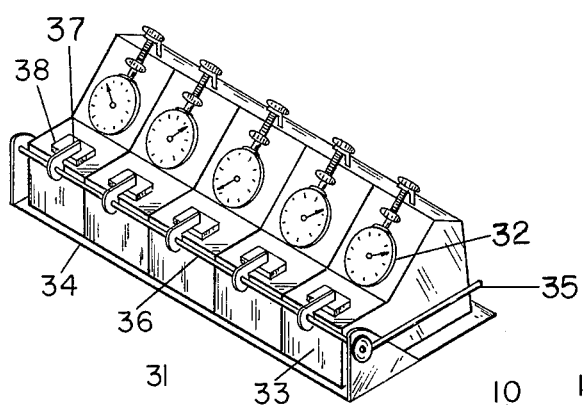
FIG. 3
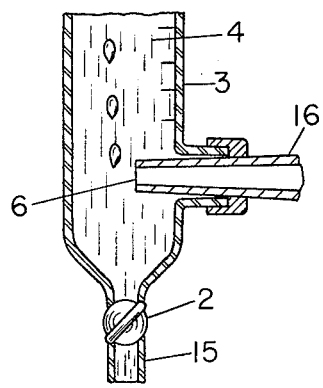
FIG. 1
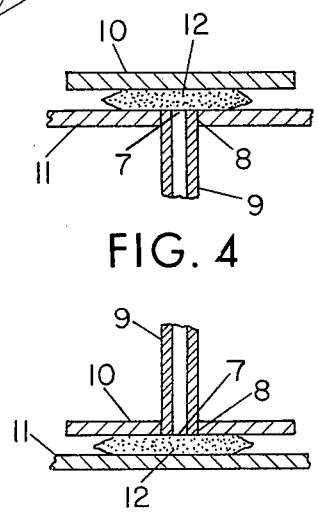
FIG. 2
FIG. 4
FIG. 5
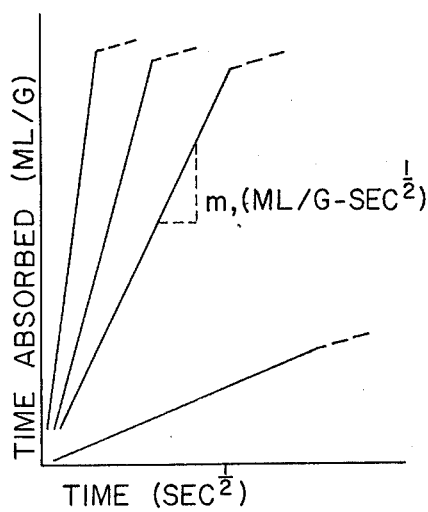
FIG. 7

MEASUREMENT OF ABSORBENCY CHARACTERISTICS OF ABSORBENT STRUCTURES

FIELD OF THE INVENTION

This invention relates generally to a device for measuring the liquid wettability or absorbency, of fibrous or other absorbent materials. Wettability or absorbency comprise both absorbent capacity and wetting rate. The absorbent capacity is measured as the volume of liquid absorbed per unit weight of the absorbent material. The wetting rate is measured as the partial capacity or volume of liquid absorbed as a function of time.

Absorbency characteristics are important determinants of the effectiveness of absorbent materials and the effectiveness of treatments to modify the surface characteristics of these materials. These characteristics are a function of both the micro and macrostructure of the absorbent material such as the capillary structure of textiles, the cellular structure of foams, the chemical structure of the component molecules, the structure of the surface of the absorbent which contacts the liquid, the chemical and physical treatment of the absorbent and the multiple plied structure of complex absorbents. It is important to be able to measure the absorbency characteristics of absorbent materials under conditions as close as possible to that of actual use. Therefore, it is desirable to be able to vary the attitude of the absorbent structure to the source of the liquid in terms of the position above or below the source of the liquid, and the angle of the absorbent to the horizontal, thereby simulating the conditions of use. It is also important to be able to measure the absorbency characteristics of absorbent materials in the configuration and state in which they are to be used, e.g., in a product having specific components, a specific number of plies or a product in the state of being under a confining pressure.

DESCRIPTION OF THE PRIOR ART

Methods for determining the wettability of absorbent structures measure separately either the rate of liquid transport or the liquid holding capacity. There is no method which measures both of these simultaneously. Wetting rate is usually measured as a rate of liquid transport, or wicking rate, as a function of the observed distance wetted. The distance wetted is detected visually. This method has been described in TAPPI Routine Control Methods, RC-8 (1950) and in Svensk Paperstidning, 74, 503 (1971). These wicking rate methods are subject to several drawbacks. Firstly, there are evaporative losses of liquid during the test. Secondly, in those tests where a dye is used to mark the liquid front, there is usually a difference between the rate of transport of the liquid and that of the dye. The difference between the advancing front of the liquid and that of the dye is large where there is a large chromatographic separation of the two by the absorbent material. Thirdly, the liquid front, detected visually, is not always related to the volume of the absorbent material being wetted. It may be only a function of the surface of the absorbent which is being observed. The difference between the volume of the absorbent material actually wetted and that observed is greatest for thick materials or for absorbent structures made up of multiple plies. Fourthly, the wicking rate technique is not easily adaptible to multiple ply structures. The plies do not predictably cohere. Fifthly, those structures which do not support themselves, such as gels and weak fibrous structures, cannot be measured with this technique. Sixthly, those methods which maintain the absorbent structure in a vertical attitude usually ignore the limiting effect of gravity on the rising fluid. This is not a valid assumption for structures containing capillaries of large diameter and for large wicking distances. And finally, only initial rates of wicking are obtained. The wicking rate profile to the point of saturation is not obtained.

Methods which measure the rate of wetting, in terms of capacity measurements, employ a porous plate to support the absorbent material. The capacities are measured as a function of the change of volume of a liquid contained in a capillary tube. Such methods are described in American Dyestuff Reporter, 31, 123 (1942), 37, 73 (1948), and 38, 397 (1949) in Textile Research Journal, 20, 239 (1950) and 37, 356 (1967). Such techniques are subject to several drawbacks. Firstly, the capillary tube offers a resistance to the movement of the liquid within it due to its own capillary pressure and to the shear and frictional forces between the liquid and the walls of the capillary. This resistance to flow changes as the amount of liquid in the capillary changes. Secondly, the porous plate itself offers a resistance to flow. The resistance to flow increases with decreasing porosity of the porous plate. Thirdly, the variable roughness of the porous plate and therefore the variable contact between the wetting surface and the absorbent material under test must also be taken into account. Fourthly, corrections for the resistances to flow of the capillary and the porous plate, and for the roughness of the porous plate, result in a large correction. The corrected rate of absorption of the absorbent material under test is obtained by taking the difference between two large numbers. The error in the resulting value is large.

Methods which measure the liquid holding capacity of an absorbent material, usually give the total capacity. Such a method is described in Testing Nonwoven Fabrics, ASTM D 1117-69. The absorbent material is submerged in the liquid or alternatively, a finite, but excess, amount of liquid is added to the absorbent material. The capacity is that amount of fluid absorbed after the excess fluid is allowed to drain off and is a function of the arbitrary amount of the time allowed for draining the sample. This method is subject to errors, related to the technique and the method of support of the sample during drainage, and to evaporative losses. Further, there is usually no way to determine the effect of confining pressures.

It is important to note that all techniques described above, require the imposition of an arbitrary amount of liquid applied at some hydrostatic head. None measure the absorbency characteristics of an absorbent material, at zero hydrostatic head, with no intervening porous structure, and where the absorbency characteristics are due only to the liquid drawing power of the absorbent material being tested. No method heretofore can conveniently measure absorbency characteristics of an absorbent material as it is incorporated into a structure of its various component parts, and as it is used, at a particular angular attitude toward the source of liquid.

SUMMARY OF THE INVENTION

It has now been discovered that a liquid can be supplied to an absorbent material in such a manner that both the liquid and the absorbent material are at atmospheric pressure and the liquid is presented to the absorbent material at a zero, negative or positive hydrostatic head. This is accomplished with a device for measuring the characteristics of materials for absorbing a liquid comprising: a liquid reservoir having an opening at its bottom and a closed air tight top; an orifice plate having a liquid delivery orifice therethrough and said liquid delivery orifice in fluid tight flow communication with said opening in said reservoir through flow communication means; an air bleed orifice in said liquid reservoir intermediate between the top and bottom thereof and in fluid communication with the atmosphere; and means for adjusting the relative heights of the air bleed orifice to the orifice plate whereby when the liquid is introduced into said liquid reservoir and fills the flow communication means, the relative height of the orifice plate to the air bleed orifice may be adjusted so that there is no fluid driving force acting to cause liquid to flow through said liquid delivery orifice and when said absorbent material is placed over said liquid delivery orifice on contact with said liquid and said liquid is drawn into said absorbent material, the fluid system will be balanced so that the absence of said absorbent material there will be no flow through said orifice plate. With this arrangement, the absorbent material can be held just close to the point where the liquid is supplied to it. At a given point in time, by a slight pressurizing of the liquid supply column, the liquid is caused to contact the absorbent. At the same moment, the time interval for liquid absorption is recorded. From the moment of contact of the liquid to the absorbent to the time at which the absorbent material has imbibed sufficient liquid to saturate it, the absorbency process proceeds spontaneously with no further pressurizing of the liquid column being required. The amount of liquid absorbed is recorded as a volume. The passage of time during the process is also recorded. The volume absorbed at any time is a partial capacity until saturation is achieved. The last value recorded is the total capacity. When the data is presented as volume absorbed as a function of time, a rate of wetting can be obtained. At any time during the process of absorbing, only that liquid demanded or drawn by the absorbent material is absorbed.

The absorbent materials can be complex, multiple plied structures which can be confined with plates over the specimen or with a surrounding frame. The absorbent material can be held at any angle from 0° to 90° to the horizontal. The absorbent material can be chosen from those solid and semisolid materials which can be contained on the apparatus of the invention. These can be chosen from such materials as textiles, foams and gels.

The liquid can be supplied to the top or to the bottom of the absorbent. The liquid can be chosen from a variety of aqueous and nonaqueous mixtures without limitation to their hydrophilic or hydrophobic nature.

It has been discovered that by practicing this invention, one can measure simultaneously both the absorbent capacity and the wetting rate of any absorbent using any liquid. It has also been discovered that the measurements can be made, although not limited to, at zero hydrostatic head.

In a specific embodiment of this invention, it is used to measure the absorbency characteristics of fibrous structures, textiles, plastic foams and gels.

BRIEF DESCRIPTION OF THE DRAWINGS

FIG. 1 is a perspective view of the device with a sample of absorbent material held between confining plates and a stopwatch assembly used for timing;

FIG. 2 is detailed, enlarged view of the air bleed to the liquid reservoir;

FIG. 3 is a detailed view of the activating mechanism for initiating wicking;

FIG. 4 is a detailed, enlarged view of the sample containing area of the device where the sample is held in a horizontal attitude and the source of liquid is below the sample;

FIG. 5 is a detailed, enlarged view of the sample containing area of the device where the sample is held in a horizontal attitude and the source of liquid is above the sample;

FIG. 6 is a detailed, enlarged view of the sample containing area of the device where the sample is held in a vertical attitude and the source of liquid is presented to the vertical side of the sample; and FIG. 7 is an example of a graph of data obtained by using this invention.

DETAILED DESCRIPTION OF THE INVENTION

Referring to FIGS. 1–4, the device shown therein comprises generally an orifice plate 11 which supports a sample of absorbent material 12 which is in turn confined by a confining plate 10. The orifice plate 11 contains within it a liquid delivery orifice 7 which communicates directly with a flow communication means comprised of a tube 9 and a connecting fitting 8. Said fitting serves to provide a liquid tight connection between orifice plate 11 and tube 9. The plate is maintained at a horizontal level by means of adjustable levelling feet 18 and 19 and spirit level 20. The flow communication means is supplied by a calibrated reservoir 3 which is attached by a connection 15 to tube 9. A valve 2 is used to regulate the liquid flow between reservoir 3 and tube 9. Said reservoir is closed by a stopper means 5 which is retained on the reservoir to provide an air tight seal during the use of the device and which is removed from the reservoir to permit filling with liquid 4. Said reservoir contains an air bleed which comprises generally an air bleed orifice 6 in a tube 16 which in turn communicates with a tube 17 via a valve 1. Attached to tube 17 is a wicking initiating mechanism which comprises generally a pressurizing means 14 and an air vent 13. A timing mechanism 31 is also provided. Also provided is a height adjusting means 39 for adjusting the relative heights of the air bleed orifice to the orifice plate.

Liquid which exits from the liquid delivery orifice 7 is continuous with that contained in the reservoir 3 and passes through the intervening components valve 2, connector 15, tube 9, and connecting fitting 8. When the liquid flows from the reservoir 3 it is replaced by air, at atmospheric pressure, from the air bleed orifice 6. The column of liquid 4 in reservoir 3 is counterbalanced by the partial vacuum in the space in the reservoir above the liquid. The resultant weight of the column of liquid 4 is equal to atmospheric pressure. If no absorbent contacts the liquid at the liquid delivery orifice, liquid will flow from said orifice only when the weight of the column of liquid in the reservoir is greater than the pressure of the atmosphere at the liquid delivery orifice. This will occur only when there is a positive hydrostatic head between the liquid delivery orifice and the air bleed orifice, i.e., when the air bleed orifice 6 is higher than the liquid delivery orifice 7. The device will then deliver fluid at a constant rate. The rate will be determined by the rate at which air is permitted to enter the reservoir through the air bleed orifice; and it will not depend on the height of the liquid column in the reservoir.

If the liquid delivery orifice 7 is at the same height as the air bleed orifice 6, or higher than said orifice 6, no liquid will flow from the liquid delivery orifice. If the device is operated at zero hydrostatic head, liquid will not issue from the liquid delivery orifice unless it is placed in contact with an absorbent material 12. Liquid will then continue to issue from the orifice until the absorbent material is saturated. When the absorbent material ceases to absorb liquid, the liquid will cease to flow. The presence of the absorbent material is equivalent to temporarily imposing a hydrostatic differential between the air bleed orifice and the liquid delivery orifice. This differential will vary only with the absorbency demand or drawing power of the absorbent material and will be independent of the height of the liquid column in the reservoir. If the device is operated at a hydrostatic head of less than zero by keeping the orifice 7 above orifice 6, no fluid will issue from orifice 7 unless forced to by pressurizing the fluid in the flow communication means so that it contacts the absorbent material. The absorbent material will then continue to absorb liquid as long as its absorbency power is sufficient to overcome the negative hydrostatic head. Under this circumstance, the absorbent will not absorb as much as it would have if the measurement was made at zero hydrostatic head.

The liquid reservoir 3 can be any container wherein the liquid level can be detected and measured by visual, optical or electronic means. The height of the liquid column above air bleed orifice 6 should not be greater than that which can be supported by atmospheric pressure when it is operated at atmospheric pressure. It is preferable to use a liquid reservoir whose internal diameter is small enough to permit small volume changes to be measured readily but not so small that the capillary space imposes excessive drag on the liquid being removed from the reservoir and on the air bubbles entering the reservoir via air bleed orifice 6 during absorbency measurements. A 25 ml buret has been found satisfactory in that it permits estimation of volume changes as small as 0.1 ml and holds sufficient liquid to saturate even several plies of rapidly absorbing material. Burets of smaller internal diameter can be used for small samples of slowly absorbing materials. Larger burets can be used for larger samples of rapidly absorbing materials where less precision of volume readings can be tolerated. Small reservoirs can also be used with highly absorbent materials by choosing small sample sizes. Thus, the reservoir capacity is chosen according to the volume of liquid absorbed at maximum capacity and the degree of precision to which volume readings must be made. Determination of the volume of the liquid absorbed is not limited to visual observation of calibration marks on the reservoir. The position of the meniscus can be detected and recorded electronically by probes at different levels when the liquid contains an electrolyte or by capacitance measurements where condenser plates are placed on the outside of the reservoir or photoelectrically where a light source and photoelectric detector are placed on the outside of the reservoir.

Any liquid of interest can be used in absorbency measurements that is compatible with the materials of construction of the device and whose viscosity is between 0.2 and 10,000 centipoise. When foaming in the reservoir liquid makes it difficult to determine the level of the liquid accurately, a small amount of antifoaming agent can be added to the liquid in the form of an emulsion, or to the top of the column of liquid in the form of an immiscible oil. The latter is used when a reduction in the surface tension of the liquid is not desired. The antifoaming agent can be one of the silicone polymers or an equivalent material usually employed for these purposes. I have used an aqueous solution of 1 g Dow-Corning, Antifoam B emulsion in 1 liter of water as the liquid in absorbency measurements. The resultant liquid has a surface tension of 46.7 dyne/cm.

The measurements are to be made at zero hydrostatic head, it is preferred that the air bleed orifice 6 and the liquid delivery orifice 7 be put at such a level relative to each other so that the liquid level in the tube is just below the liquid delivery orifice 7, e.g., about 1 mm or less below the orifice. In this manner wicking is not initiated immediately on placing the sample over the orifice but instead only when wicking is intentionally initiated at the beginning of the absorbency measurement using the wicking initiating mechanism. The orifice 7 is continuous with a connecting means 8 which forms an air tight seal between itself and the plate 11. The connecting means are connected to tube 15 by a tube 9 which is preferably flexible to permit raising and lowering the relative levels of orifices 6 and 7 and adjustment of the angle to the horizontal of orifice plate 11. The smallest internal diameter of any of the parts of the connecting tubing 9 and the parts connected, 3, 2, 15, 8 and 7, should preferably not be less than 2 mm. The minimum diameters of choice are 3–5 mm. These diameters of the apparatus permit flow to a small area of the sample without permitting the dimensions of the apparatus to be the limiting factor in determining the rate of flow of liquid to the absorbent material. The liquid delivery orifice 7 need not be circular. It may be shaped like a cross, a line, a square, a rectangle, an oval or any other plane geometric shape. Larger areas of absorbent material can be subjected to wetting by employing a larger delivery orifice. For example, one may require a line-shaped orifice to determine the absorbency characteristics of a surgical dressing material when it is applied to an incision. Similar considerations can be applied to determine the dimensions of the air bleed. The diameter of the air bleed orifice 6 should not be so large as to permit growth of large bubbles of air before they are bled into the liquid nor should they be so small that they become the limiting factor in the rate of flow of the liquid to the absorbent material. The air bleed and its orifice need not be circular in cross section. Gases other than air may also be used.

The orifice plate 11 can be either the bottom or the top plate depending on the direction which it is preferred to supply the fluid to the absorbent material. The confining plate 10 and orifice plate 11 can be made of any material which will uniformly and reproducibly confine the absorbent material under test. It is preferred that the plates be made of a flat, solid, material such as metal, glass, plastic or rubber. It is further preferred that the surface be of uniform smoothness so that contact between the plates and the absorbent material is uniform, reproducible and as complete as possible. It is also further preferred that the plates be fabricated from a material with a nonwettable coating such that the surface energy of the plate is less than that of the liquid being employed. Examples of such surfaces, but not limited to those mentioned herein, are polytetrafluoroethylene, polyethylene, polypropylene, polyvinylidine fluoride, polychlorotrifluoroethylene and neoprene rubber. A nonwettable surface is preferred since it minimizes the quantity of liquid which is absorbed in the capillary spaces which are formed between the plates and the absorbent material. It should be noted, however, that any surface can be used and that the apparent absorbent capacity obtained with a given liquid and absorbent system may increase with increased wettability of the surfaces of the plates. Thus, it was noted that the absorbent capacity of a given absorbent material for water, using a fixed confining plate weight, increased as the plates were changed from both polytetrafluoroethylene to one polytetrafluoroethylene and one polymethylmethacrylate to both polymethylethacrylate to both glass. The plates can be of any size and weight. It is preferred that the diameter of the upper plate be not much larger than that of the sample so that it does not lean nonuniformly on the surface of the absorbent material. The confining weight of the upper plate can be changed by the use of a heavier plate or by the addition of more plates on top of the first one or by an external pressurizing means such as a hydraulic piston device. A hydraulic piston device is particularly useful when the absorbent material is tested in a non-horizontal position as is shown in FIG. 6.

If desired, the plates can be separated at a fixed distance from each other by an arrangement of spacers and confining screws so as to prevent the absorbent material from being compressed continuously after being confined initially. Also, if desired, no upper plate need be employed. Referring to FIG. 6, the plate assembly may be tilted to enable testing the absorbency of the absorbent material at angles from 0° to 90° to the horizontal. When the angle of the assembly is so much greater than 0°, so as to make it difficult to maintain the absorbent material sample and the retaining plate in a fixed position relative to the other supporting plate, an external securing and pressurizing means can be used to accomplish this end. As best shown in FIG. 6, this can be accomplished by attaching the orifice plate 21 to a tilting means 22 so that said plate can be turned to any attitude from 0° to 90° to the horizontal and kept at a given angle by a locking means 23. The confining plate 24 can be held in place by guiding pins 25 and 26 which are attached to plate 21 and pass through holes 27 and 28 and can be held against the absorbent material by a pressurizing means 29 such as a hydraulic piston device. The pressure of the confining plate 24 against the sample of absorbent material can be varied by changing the force of the hydraulic piston device which is exerted against said plate. A pressure indicating means such as a gauge 30 can be used to indicate the pressure which the pressurizing means is exerting on the sample of absorbent material.

The absorbent material can be any solid or semisolid which can be contained between the confining plate 10 and orifice plate 11 and which is not dissolved by the liquid used in the absorbency measurement. The absorbent material can be in the form of a woven or formed textile, paper, pad of loose fibers, foam, powder or gel. Absorbent materials which are not self adherent, tend to be disrupted by the liquid, can be confined by a thin ring held between the plates. Absorbent materials can be tested in single or multiple plied arrangements. The absorbent material can be in a composite form such as a dressing, bandage, catamenial sanitary napkin, tampon, diaper, incontinence pad, urethane sponge and scrim reinforced construction. Several samples, one on the other, may be tested at the same time. Relatively non-absorbent materials may also be tested. These may be used to determine the relative wetting ability of different liquids. An example would be the measurement of the ability of aqueous solutions, containing different wetting agents, to wet relatively hydrophobic textiles made of fibers such as wool or polyester. Another example would be the measurement of the effectiveness of certain treatments to change the wetting characteristics of absorbent. Examples of such treatments are corona discharge, grafting of polyacrylic acid, water and stain repellents and wetting agents. The sample of absorbent material can be any shape such as circular, oval, square, rectangular and the like. These can be cut using any convenient means such as shears, cutting board and cutting die.

Referring to FIG. 1, a convenient timing mechanism 31 has been found to be a bank of five to ten stopwatches which are so arranged that all the watches can be activated by a single lever at the initiation of wicking. Each watch 32 is held in a stopwatch holder 33, such as Fisher Scientific No. 14-651-5. The holders, in turn, are bolted to a single plate 34 to which is also attached the activating lever 35 and the bar 36 containing the rods 37 which activate each watch. At each of several convenient volume readings, a watch is stopped by depressing the individual control lever 38 for that watch. The individual control levers can be operated without the need for their direct observation. In this way, the operator need only observe the volume changes in the reservoir. At the end of the test, the time readings are recorded.

The height adjusting means 39 can be any device which permits adjusting the relative height of the air bleed orifice to the orifice plate and retaining the desired relative height by securing or clamping.

Referring to FIGS. 1 to 4, the device is used by first having the valves 1 and 2 closed and the stopper means 5 removed. The liquid reservoir 3 is filled with liquid and the stopper means is replaced. The device is adjusted so that the orifices 6 and 7 are at about the same height. With the valves 1 and 2 open, the relative height of the orifices are further adjusted so that the liquid is about 1 mm or less below the orifice 7 at the surface of plate 11. Liquid is removed from all parts which connect the activating mechanism to the tip of the air bleed. Liquid is also removed from the reservoir until the liquid is drained to some convenient height. Removal of liquid is accomplished in each instance by placing an absorbent material such as paper toweling over the liquid delivery orifice. Referring to FIG. 3 wicking is initiated by momentarily closing off the tube 13 while gently squeezing the rubber bulb 14. Alternatively, wicking can be initiated by changing the relative height of plate 10 to that of plate 11 so that a slight hydrostatic head is obtained so that liquid issues from orifice 7 sufficiently to contact the absorbent material 12. Wicking is halted merely by removing the absorbent material.

A sample of absorbent 12 is cut, conditioned at some requisite temperature and humidity, and weighed. The upper confining plate of desired weight is placed on the sample. Wicking is initiated as above. The rubber bulb is released as soon as wicking begins. At the instant of initiation of wicking, the timing mechanism is started by depressing the lever which activates all the watches simultaneously. During the absorption process, liquid which is withdrawn from the reservoir is replaced by air. Volume and time readings are recorded for as long as the absorption process occurs. Absorption stops when the absorbent material is saturated with liquid. At this point, liquid no longer flows from the reservoir; air ceases to enter the reservoir via the air bleed. Replicate samples are measured in the same manner. Three to five replicates are usually measured. During the absorption process, air travelling between the air bleed orifice and the top of the liquid column in the reservoir, displaces its own volume thereby giving a volume reading less than has been actually withdrawn. This can also be viewed as the time elapsed being greater than is actually required to absorb the observed volume. A convenient method of correction is to measure the time required for an air bubble to rise from the air bleed orifice to the top of the liquid column in the reservoir as a function of the height of the liquid column. A calibration curve is drawn for each buret/fluid combination. Corrections in terms of time are obtained for every buret liquid level reading. These corrections are subtracted from the observed time readings.

The raw data is obtained as the volume of liquid absorbed (ml) as a function of time (seconds or minutes). The time readings are corrected as above. Nonuniformities among samples of a given absorbent material are normalized by dividing or multiplying the absorbed volumes by the weight of the sample. If the absorbed volume is divided by the weight of the sample, the normalized volume is expressed as ml liquid/g sample. The total absorbent capacity is the final volume recorded when the material stops absorbing. A plot of the absorbent capacity as a function of (time)$^{1/2}$ usually yields a linear plot for the entire range of data except perhaps for the last point. This point represents the last fraction of liquid required to saturate the sample. The fraction of the total absorbent capacity which falls on the straight line is 25% to almost 100%. This fraction depends on the absorbency characteristics of the sample and the number of watches available for timing. The slope of the straight line portion of the plot, of ml/g vs (time)$^{1/2}$, is denoted by $m$. It is expressed as ml/(g-sec$^{1/2}$). It is related to the average wetting rate over the whole range of data. The wetting rate at a particular time, $t_n$, is given by the relationship $m/2(t_n)^{1/2}$.

This is an instantaneous rate which can be used, for example, to differentiate absorbents which show rapid absorption initially, but fail badly in the last stages of absorption, from those that maintain a rapid rate throughout.

EXAMPLES OF DATA OBTAINED WITH THIS INVENTION

The following are merely illustrative of the present invention, and should not be considered as limiting the scope of the invention in any way, as these examples and other equivalents thereof will become apparent to those versed in the art in light of the present disclosure, drawings and accompanying claims.

FIG. 7 shows a graph of data obtained on absorbent materials using this device and method. Table I is a summary of the absorbency characteristics obtained on needled rayons of different fabric weights. Table II is a summary of absorbency characteristics of a rayon fabric as function of the number of plies and as a function of confining weight.

TABLE I.

ABSORBENCY CHARACTERISTICS OF NEEDLED RAYONS AS A FUNCTION OF FABRIC WEIGHT

| Weight (oz/yd$^2$) | Ave. Rate (ml/g-sec$^{1/2}$) | Capacity (ml/g) |
|---|---|---|
| 2.35 | 2.33 | 12.2 |
| 5.1 | 2.29 | 11.1 |
| 6.1 | 2.50 | 11.6 |
| 9.0 | 1.83 | 11.4 |

TABLE II

VARIATION OF ABSORBENCY CHARACTERISTICS WITH NUMBER OF PLIES AND WITH CONFINING WEIGHT (100% RAYON, NONWOVEN, 1.0 OZ/YD$^2$)

| PRESSURE (g/cm$^2$) → | 5.12 | 9.27 | 13.57 | 17.81 | 5.12 | 9.27 | 13.57 | 17.81 |
|---|---|---|---|---|---|---|---|---|
| NO. OF PLIES ↓ | CAPACITY (ml/g) | | | | AVE. RATE (ml/g-sec$^{1/2}$) | | | |
| 10 | 9.2 | 7.7 | 6.9 | 6.6 | 1.09 | 0.81 | 0.90 | 0.78 |
| 5 | 8.1 | 7.4 | 6.9 | 6.4 | 1.29 | 1.00 | 1.00 | 0.95 |
| 2 | 7.9 | 7.1 | 6.8 | 6.4 | 1.49 | 1.14 | 0.83 | 0.91 |
| 1 | 8.3 | 7.6 | 7.1 | 6.4 | 1.46 | 1.18 | 0.92 | 0.91 |

The novel device of this invention employs a unique means for permitting the measurement of absorbency characteristics, of absorbent capacity and of wetting rate, of absorbent materials as a function of the drawing power for liquid exhibited by the absorbent material and in a manner which is directly related to the mode of intended use of the absorbent material. While there has been described and pointed out the fundamental novel features of the invention as applied to the presently preferred embodiments, those skilled in the art will appreciate that various modifications, changes and omissions in the absorbency characteristics measuring devices and the methods for their use illustrated and described can be made without departing from the spirit of the invention.

I claim:

1. A device for measuring the characteristics of materials for absorbing a liquid comprising: a liquid reservoir having an opening at its bottom and a closed air tight top; an orifice plate having a liquid delivery orifice therethrough and said liquid delivery orifice in fluid tight flow communication with said opening in said reservoir through flow communication means; an air bleed orifice in said liquid reservoir intermediate between the top and bottom thereof and in fluid communication with the atmosphere; and means for adjusting the relative heights of the air bleed orifice to the orifice plate whereby when the liquid is introduced into said liquid reservoir and fills the flow communication means, the relative height of the orifice plate to the air bleed orifice may be adjusted so that there is no fluid driving force acting to cause liquid to flow through said liquid delivery orifice and when said absorbent material is placed over said liquid delivery orifice in contact with said liquid and said liquid is drawn into said absorbent material, the fluid system will be balanced so that in the absence of said absorbent material there will be no flow through said orifice plate.

2. The device of claim 1 wherein a means is provided for holding said absorbent material at any angle from 0° to 90° to the horizontal.

3. The device of claim 1 wherein a means is provided for applying said liquid delivery orifice to the top or to the bottom of said absorbent material.

4. The device of claim 1 wherein the hydrostatic head of said liquid being applied to said absorbent material is zero.

5. The device of claim 1 wherein the hydrostatic head of the liquid being applied to said absorbent material is greater or less than zero.

6. The device of claim 1 wherein said absorbent material is a multiple plied structure.

7. The device of claim 1 wherein said absorbent material is confined by a weight or pressurizing means.

8. The device of claim 1 wherein said absorbent material is a textile, fibrous pad, foam or gel.

9. The device of claim 1 wherein a means is provided for determining the volume of said liquid contained within said reservoir.

10. The device of claim 1 wherein said liquid has a viscosity of 0.2 to 10,000 centipoises and any surface tension.

11. The device of claim 10 wherein said liquid contains an antifoaming agent.

\* \* \* \* \*